(12) United States Patent
Leung et al.

(10) Patent No.: US 10,173,033 B2
(45) Date of Patent: Jan. 8, 2019

(54) IMAGING MARKER

(71) Applicant: Baylis Medical Company Inc., Montreal (CA)

(72) Inventors: Linus Hoi Che Leung, Toronto (CA); John Paul Urbanski, Toronto (CA); Glenn Arnold, Mississauga (CA)

(73) Assignee: Baylis Medical Company Inc., Montreal, Quebec (CA)

(*) Notice: Subject to any disclaimer, the term of this patent is extended or adjusted under 35 U.S.C. 154(b) by 136 days.

(21) Appl. No.: 15/131,093

(22) Filed: Apr. 18, 2016

(65) Prior Publication Data

US 2016/0303348 A1    Oct. 20, 2016

Related U.S. Application Data

(60) Provisional application No. 62/148,410, filed on Apr. 16, 2015.

(51) Int. Cl.
  *A61M 25/01* (2006.01)
  *A61B 90/00* (2016.01)

(52) U.S. Cl.
  CPC ......... *A61M 25/0108* (2013.01); *A61B 90/39* (2016.02); *A61B 2090/3966* (2016.02)

(58) Field of Classification Search
  CPC ....... A61M 25/0108; A61B 2090/3966; A61B 90/39
  See application file for complete search history.

(56) References Cited

U.S. PATENT DOCUMENTS

| | | | |
|---|---|---|---|
| 4,774,949 A | 10/1988 | Fogarty | |
| 5,203,777 A | 4/1993 | Lee | |
| 6,520,934 B1* | 2/2003 | Lee | A61M 25/0108 604/103.1 |
| 6,648,854 B1* | 11/2003 | Patterson | A61M 25/005 604/524 |
| 6,733,489 B2 | 5/2004 | Nutting et al. | |
| 7,153,277 B2* | 12/2006 | Skujins | A61M 25/09 600/585 |
| 8,374,680 B2* | 2/2013 | Thompson | A61B 17/3207 600/424 |
| 2008/0097404 A1 | 4/2008 | Yribarren et al. | |
| 2013/0158507 A1* | 6/2013 | Brown | A61M 25/007 604/506 |
| 2013/0197353 A1* | 8/2013 | Von Oepen | A61M 25/0108 600/424 |
| 2013/0245430 A1* | 9/2013 | Selmon | A61B 6/12 600/424 |

* cited by examiner

*Primary Examiner* — Quynh-Nhu H Vu
(74) *Attorney, Agent, or Firm* — Nir Lifshitz; Glenn Arnold; Vincent Man

(57) ABSTRACT

An imaging marker for use with a catheter, the imaging marker comprising a plurality of segments including at least two stiff segments and at least one flexible segment, wherein for each pair of stiff segments, one of the flexible segments is located therebetween such that the flexible segment is operable to function as a hinge when the imaging marker is bent. In typical embodiments, the stiff segments are visible under a medical imaging system. In some embodiments, the stiff segments are comprised of a radiopaque material which is visible under an X-ray (fluoroscopy) imaging system.

22 Claims, 3 Drawing Sheets

IMAGING MARKER

CROSS-REFERENCES TO RELATED APPLICATIONS

This application claims the benefit of U.S. provisional application No. 62/148,410, filed on Apr. 16, 2015, which is incorporated-by-reference herein in its entirety

TECHNICAL FIELD

The disclosure relates to the field of medical devices. More specifically, the disclosure relates to imaging markers used in medical devices.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
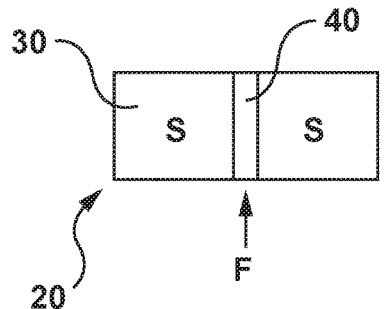
FIG. 1A is a top view of an imaging marker with two stiff segments in accordance with an embodiment of the present invention.

A side-port of a catheter decreases the stiffness of the catheter's shaft since a portion of the catheter's material is removed to define the side-port. This decreased shaft stiffness results in a stiffness profile with abrupt changes, which may make it more challenging to advance a catheter, or any elongated medical device, through tortuous anatomy. In some cases, a non-gradual transition of shaft stiffness leads to difficulty in tracking up and over the aorta-iliac bifurcation. In some particular cases, as the distal tip of a catheter advances across the bifurcation, the catheter shaft proximal to the side-port advances up the aorta, creating a U-shaped bend in the shaft. In instances where the catheter has a solid imaging marker extending the length of the side-port (e.g. a platinum marker), the U-shaped bend can deform or kink the marker permanently. Such deformations may prevent the catheter from returning to its original shape when the catheter is retracted. It is more difficult to advance or withdraw a deformed catheter than an undamaged catheter, especially through tortuous paths. A marker for marking the entire length of a long side-port (e.g. a capsule shaped side-port) is especially vulnerable to such damage.

The present inventors have conceived and reduced to practice multiple embodiments of imaging markers that reduce, minimize or alleviate such undesirable deformations. Typically, embodiments of the present invention include imaging markers comprised of alternating stiff segments and flexible segments wherein at least two of the segments are stiff segments. Alternating segments of the marker may comprise more than one material to provide sufficient flexibility to avoid permanent kinking. In typical embodiments, the stiff segments are comprised of a material visible under a medical imaging system. In some such embodiments, the stiff segments are comprised of a radiopaque material which is visible under an X-ray (fluoroscopy) imaging system.

The disclosed imaging marker may be used in a device without a side-port. In a device with a side-port, the imaging marker provides support to the portion of the catheter having the side-port.

In one broad aspect, embodiments of the present invention comprise an imaging marker for use with a catheter, the imaging marker comprising a plurality of segments including at least two stiff segments and at least one flexible segment, wherein for each pair of the at least two stiff segments, one of the one or more flexible segments is located therebetween such that the flexible segment is operable to function as a hinge when the imaging marker is bent.

In a further broad aspect, embodiments of the present invention comprise a catheter comprising at least one imaging marker, the at least one imaging marker comprising a plurality of segments including at least two stiff segments and at least one flexible segment, wherein for each pair of the at least two stiff segments, one of the one or more flexible segments is located therebetween such that the flexible segment is operable to function as a hinge when the catheter is bent at a location of the imaging marker. As a feature of this aspect, a portion of the catheter includes a side-port and the segmented imaging marker is operable to mark the position of the side-port.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Embodiments of the present invention provide a segmented imaging marker that can bend and flex without permanent deformation when it is advanced and withdrawn through torturous anatomy.

Figure 1B:
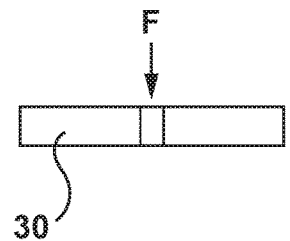
FIG. 1B is a side view of the imaging marker of FIG. 1A.

FIGS. 1A and 1B show top and a side views, respectively, of an example of an imaging marker with one flexible segment 40 between two stiff segments 30. In the drawings, stiff segments are indicated by an "S" and flexible by an "F". A stiff segment 30 of FIGS. 1A and 1B is visible under imaging. In typical embodiments, stiff segment 30 is comprised of a radiopaque material such as platinum and flexible segment 40 is comprised of a flexible non-radiopaque material, typically a polymer. This configuration allows flexible segment 40 to function as a hinge such that the marker may bend without permanent deformation. In typical embodiments, stiff segments 30 and flexible segment 40 are pre-joined to facilitate easier installation during the assembly of a medical device such as a catheter.

In some embodiments, stiff segment 30 is comprised of a radiopaque material, while in some alternative embodiments, stiff segment 30 is covered with a radiopaque coating. The radiopaque material of the stiff segment is selected from the group consisting of platinum, iridium, gold, palladium, tungsten, or alloys thereof. In some embodiments, the radiopaque material is comprised of about 90% platinum and about 10% iridium. In alternative embodiments, the radiopaque material is comprised of about 92% platinum and about 8% tungsten. In some alternative embodiments, stiff segment 30 is comprised of a radiopaque polymer. In general, an imaging marker 20 comprised of metal is stiffer and provides better support than a polymer marker, particularly in cases where the imaging marker is located at side-port. Further details regarding materials used in radiopaque markers are found in PCT application PCT/IB2012/056315, entitled "Radiofrequency perforation apparatus", filed Nov. 9, 2012, which is herein incorporated-by-reference in its entirety.

In some alternative embodiments, stiff segment 30 is visible under ultrasound or magnetic resonance imaging (MRI) imaging systems. Examples of means to provide imaging include magnetic components including magnetic coils for MRI, and surface markings in the case of ultrasound. Further details regarding materials and means used in magnetic and echogenic markers are found in U.S. application Ser. No. 13/962,396, entitled "Medical devices with visibility-enhancing features", filed Aug. 8, 2013, which is herein incorporated-by-reference in its entirety.

In some alternative embodiments, flexible segment 40 is comprised of a radiopaque polymer, for example, a polymer containing a radiopaque powder such as is known to those skilled in the art. In some alternative embodiments, flexible segment 40 is comprised of a thin metal layer which is the same material as stiff segment 30, while in some other alternative embodiments, flexible segment 40 is comprised of a different metal. In yet another alternative embodiment, flexible segment 40 is comprised of a mechanical hinge. In some alternative embodiments, stiff segment 30 and/or flexible segment 40 are comprised of braided materials.

Figure 2:
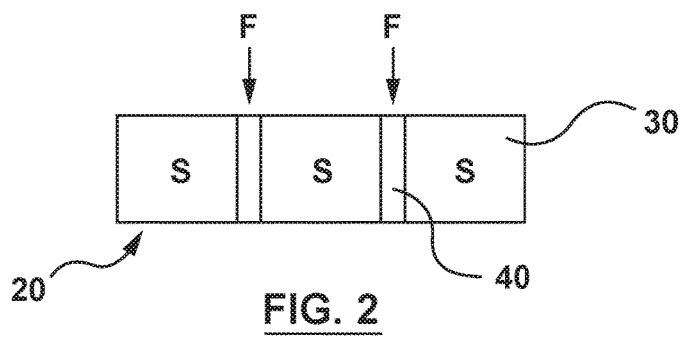
FIG. 2 is a top view of an imaging marker with three stiff segments in accordance with an embodiment of the present invention.

FIG. 2 illustrates an embodiment of the present invention comprising imaging marker 20 having three stiff segments 30 and two flexible segments 40. Increasing the number of segments for an imaging marker 20, while keeping the marker's length constant, provides more flexibility for travelling through tortuous paths. Conversely, decreasing the number of segments for an imaging marker 20, while keeping the marker's length constant, provides greater stiffness and support, which is particularly relevant when the marker is at a side-port, especially if the side-port is longitudinally elongate. In general, the number of segments can be selected to adjust the stiffness profile appropriate for the application. In typical embodiments, the stiff sections are close enough that they appear as a single marker under imaging. Further embodiments may include more than three stiff segments 30.

Figure 3:
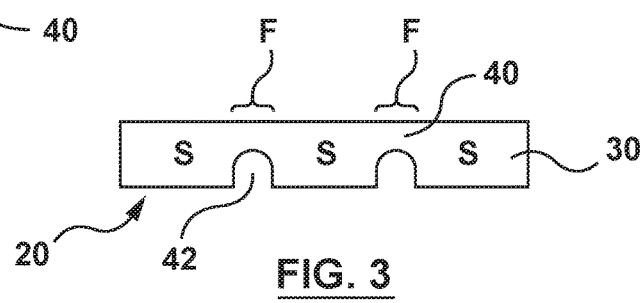
FIG. 3 is a side view of an imaging marker with two cut-out flexible segments in accordance with an embodiment of the present invention.

FIG. 3 is a side view of an embodiment of an imaging marker 20 with two flexible segments 40. Some embodiments of imaging marker 20 are substantially comprised of one material, and flexible segments are defined by areas where some of the material has been removed, creating cut-out portions 42. Cut-out portions 42 can be formed by cutting into the material (or materials, in the case of alternative embodiments) of imaging marker 20 with a laser or some other means.

Figure 4:
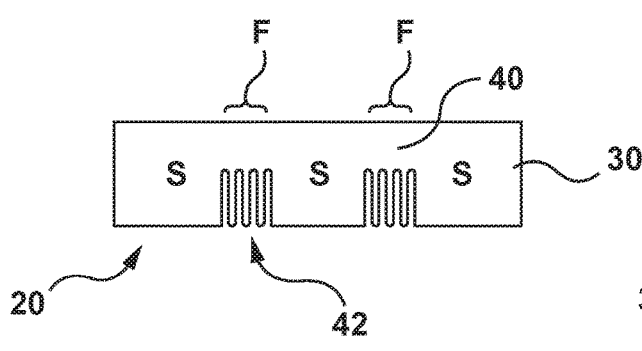
FIG. 4 is a side view of an alternative embodiment of an imaging marker with two cut-out flexible segments.

FIG. 4 is a side view of an embodiment of an imaging marker 20 with two flexible segments 40 similar to the embodiment of FIG. 3. In this embodiment, cut-out portions 42 include multiple relatively smaller cut-outs rather than a single cut-out.

Figure 5:
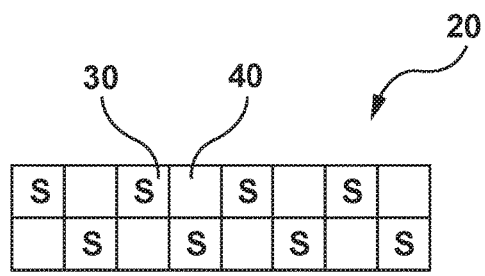
FIG. 5 is a top view of an imaging marker with multiple stiff and flexible segments in accordance with an embodiment of the present invention.

The embodiment shown in FIG. 5 includes multiple stiff segments 30 and flexible segments 40 arranged in two longitudinal rows which provide flexibility longitudinally and laterally. Further embodiments include more than two longitudinal rows.

Figure 6:
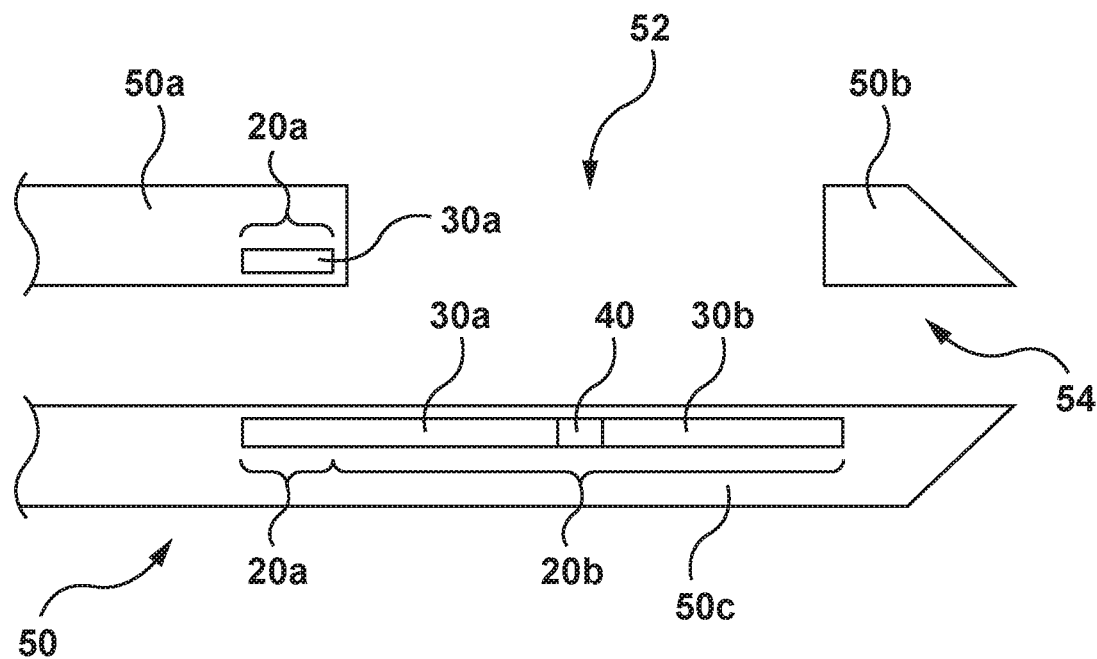
FIG. 6 is a cross-sectional side view of a catheter having an imaging marker comprising two stiff segments in accordance with an embodiment of the present invention.

FIG. 6 illustrates a cross-sectional side view of an embodiment of a catheter 50 having an imaging marker with two stiff segments. Catheter 50, indicated by 50a, 50b, and 50c, includes a side-port 52 and a lumen 54. The imaging marker, indicated by stiff segment 30a, flexible segment 40, and stiff segment 30b, is located at side-port 52 with at least of portion of the imaging marker opposite to the side-port. Imaging marker 20 is longitudinally orientated with respect to catheter 50. In some embodiments, flexible segment 40 is comprised of the same material as the side wall of catheter 50, typically a polymer. In some alternative embodiments, flexible segment 40 comprises a void (i.e. an empty space) surrounded or defined by a polymer which may be a different polymer than the side wall. Flexible segment 40 acts as a hinge and allows the side-port to bend while tracking through tortuous anatomy. Typically, stiff segment 30a and stiff segment 30b are close enough that the two segments appear as a single marker under imaging.

Figure 7:
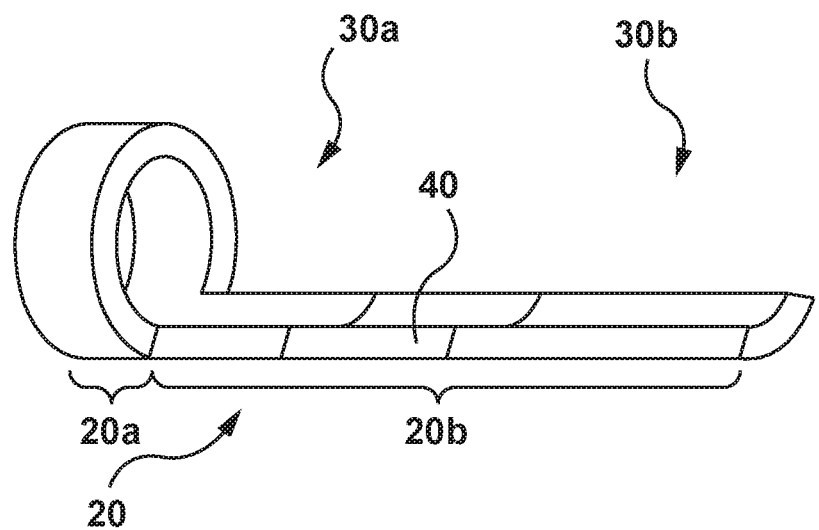
FIG. 7 is a perspective view of the imaging marker of FIG. 6.

FIG. 7 illustrates a perspective view of the imaging marker 20 of FIG. 6, comprising stiff segments 30a and 30b. When viewed under imaging from above, imaging marker 20 appears as a "T" shape, and when viewed under imaging from the side, imaging marker 20 appears as an "L" shape. Such markers are known as "LT" markers. The marker backbone 20b of FIG. 7 has a curved configuration for corresponding with a side wall of a catheter. Marker band 20a of FIGS. 6 and 7 has a generally circular cross section which substantially corresponds with a cross section of the side wall of the catheter 50 for embedding the imaging marker within the side wall of the catheter.

Imaging marker 20, which is typically includes a metal, provides additional support at the portion of catheter 50 having side-port 52 while allowing the catheter to bend and flex when travelling through curves without permanent deformation of imaging marker 20. The embodiments of imaging marker 20 of FIGS. 6 to 8 further include a marker band 20a and marker backbone 20b which may be used to visualize the location of side-port 52 under imaging. Imaging marker 20 is typically comprised of a radiopaque metal, for example, stainless steel, platinum, or a mixture of platinum and iridium. A proximal portion of imaging marker 20, marker band 20a, is typically located proximal of side-port 52 such that marker band 20a may be used to facilitate determination of longitudinal positioning of side-port 52. Marker backbone 20b is substantially opposite to side-port 52, i.e. aligned at about 180° relative to the side-port, such that marker backbone 20b is operable to facilitate determination of a rotational orientation of side-port 52. Marker backbone 20b may also be used for longitudinal positioning. Further details regarding providing support while allowing flexibility are disclosed in U.S. provisional application 61/929,158, entitled "Collapsible Tip Re-entry Catheter", filed Jan. 20, 2014, and in PCT application PCT/IB2015/050396, entitled "Collapsible Tip Re-entry Catheter", filed Jan. 19, 2015, both of which are herein incorporated-by-reference in their entirety.

While the embodiment of imaging marker 20 of FIG. 6 and FIG. 7 is comprised of two stiff segments, some alternative embodiments are comprised of three stiff segments. Dimensions of some embodiments having two or three stiff segments for use with an embodiment of side-port 52 of about 7 mm in length are shown in the following table:

| Feature/Property | Nominal value | Workable range |
| --- | --- | --- |
| Young's modulus of stiff segment 30 | 170 Gpa | ≈100-400 GPa (typical range for metals) |
| Young's modulus of flexible segment 40 | 0.8 GPa | 0.5-4 GPa |
| Length of catheter 50 | 1.2 m | 1-1.5 m |
| Total length of imaging marker 20 | about 7 mm for a reduced-length imaging marker [Otherwise, about 8 mm for 2 stiff segments, about 9 mm for 3 stiff segments] | 5-15 mm |
| Length of stiff segment 30 in a 2-segment configuration | 3.5 mm | 2-7.5 mm |
| Length of flexible segment 40 in a 2-segment and 3-segment configuration | 1 mm | 0.5-2 mm |
| Length of stiff segment 30 in a 3-segment configuration | 2.3 mm | 1.5-5 mm |

Regarding the total length of imaging marker 20, the dimensions of stiff segment 30 and flexible segment 40 can be reduced to combine for a total length of imaging marker of about 7 mm, which is the nominal size of the side-port. Alternately, the total length of imaging marker may be about 8 mm for markers with two stiff segments, and about 9 mm for markers with three stiff segments. Typically, the stiff segments are close enough that the segments may function as a single marker under imaging. Such imaging markers could possibly be used in a re-entry catheter.

In typical embodiments, stiff segment 30a and stiff segment 30b are pre-joined by a flexible material to facilitate easier loading during device assembly. The material comprising flexible segment 40 may be the same type of material as the side-wall of catheter 50 or, in alternative embodiments, may be a different material. Other alternative embodiments of the imaging marker of FIGS. 6 and 7 include flexible segment 40 being comprised of the previously described embodiments of flexible segment 40 of FIGS. 1 to 5. A flexible segment 40 may or may not be radiopaque.

Figure 8:
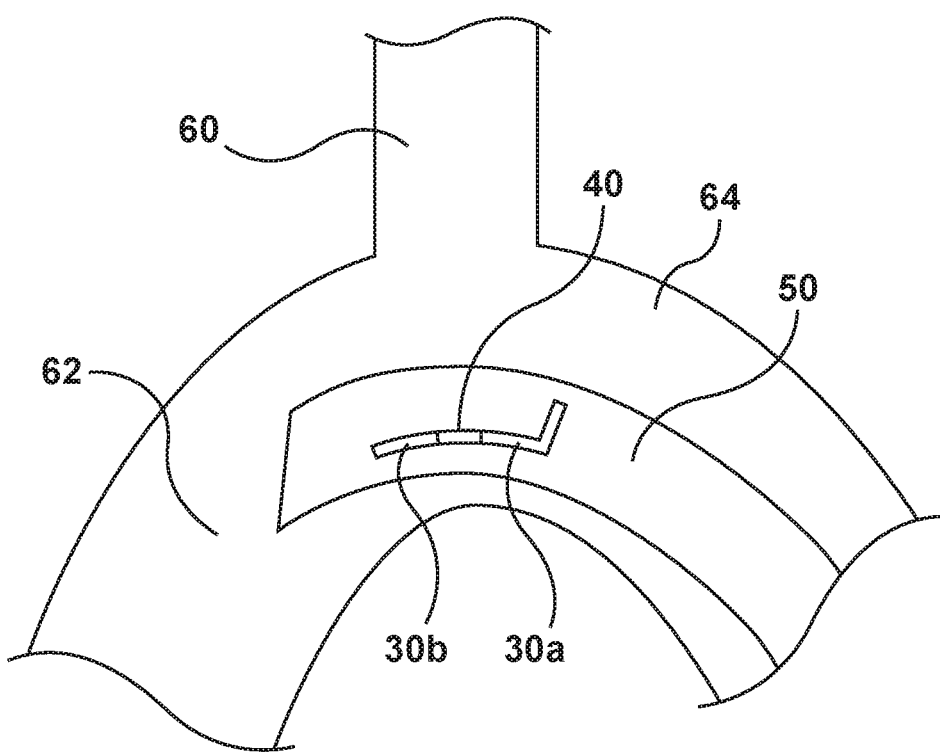
FIG. 8 is diagrammatic cross-section of a catheter with an imaging marker with two stiff segments traversing an aorta-iliac bifurcation.

FIG. 8 illustrates catheter 50, similar to the embodiment of FIG. 6, traversing an aorta-iliac bifurcation, defined by the abdominal aorta 60, right common iliac artery 62, and left common iliac artery 64. Flexible segment 40 bends with the catheter allowing independent movement of stiff segment 30a and stiff segment 30b. As a result, catheter 50 traverses the aorta-iliac bifurcation without permanent deformation of the imaging marker.

In further embodiments of the present invention, imaging markers described herein may be used in devices other than catheters and in devices without a side-port. For example, the disclosed imaging markers may be used in devices used in epicardial procedures. Embodiments of the present invention are suitable for use in any type of medical device that travels through tortuous anatomy.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An imaging marker for use with a catheter, the imaging marker comprising a marker band and an elongate marker backbone, the elongate marker backbone comprising a plurality of segments including at least two stiff segments substantially comprised of a first material and at least one flexible segment substantially comprised of a second material, wherein for a pair of the at least two stiff segments, one of the at least one flexible segments is-located therebetween such that the flexible segment is operable to function as a hinge when the imaging marker is bent.

2. The imaging marker of claim 1, wherein the stiff segments are radiopaque and the at least one flexible segment is not radiopaque.

3. The imaging marker of claim 2, wherein the stiff segments comprise material selected from the group consisting of platinum, iridium, gold, palladium, tungsten, and alloys thereof.

4. The imaging marker of claim 2, wherein the stiff segments are comprised of a radiopaque polymer.

5. The imaging marker of claim 2, the second material is more flexible than the first material.

6. The imaging marker of claim 2, wherein the flexible segment is not radiopaque and wherein the stiff segments are about 0.5 to 2 mm apart.

7. The imaging marker of claim 1, wherein the plurality of segments comprise the two stiff segments with the one flexible segment therebetween.

8. The imaging marker of claim 1, wherein the flexible segment is comprised of a polymer and the at least two stiff segments are comprised of a metal.

9. The imaging marker of claim 8, wherein the polymer is not radiopaque.

10. The imaging marker of claim 1, wherein the flexible segment is comprised of a braided material.

11. The imaging marker of claim 1, wherein the marker bands comprised of same material as the at least two stiff segments of the marker backbone, and the marker band and the one of the at least two stiff segments are continuous.

12. The imaging marker of claim 11, wherein the marker backbone has a cross section with a curved configuration for corresponding with a side wall of a catheter.

13. The imaging marker of claim 1, wherein the marker band has a generally circular cross section.

14. A catheter comprising at least one imaging marker, the at least one imaging marker comprising a marker band and an elongate marker backbone, the elongate marker backbone comprising a plurality of segments including at least two stiff segments substantially comprised of a first material and at least one flexible segment substantially comprised of a second material, wherein for a pair of the at least two stiff segments, one of the at least one flexible segments is located therebetween such that the flexible segment is operable to function as a hinge when the catheter is bent at a location of the imaging marker.

15. The catheter of claim 14, wherein the second material is more flexible than the first material.

16. The catheter of claim 14, further comprising a side wall defining a side-port, and wherein the elongate marker backbone is associated with a portion of the side wall opposite the side-port such that the elongate marker backbone provides support to a portion of the catheter having the side-port.

17. The catheter of claim 16, wherein the imaging marker is embedded in the side wall.

18. The catheter of claim 16, wherein the imaging marker is attached to a surface of the side wall.

19. The catheter of claim 16, wherein the side-port is longitudinally elongate and the marker backbone is located substantially parallel to and opposite the side-port wherein the marker backbone is operable to facilitate determination of a rotational orientation of the side-port.

20. The catheter of claim 16, wherein a proximal portion of the imaging marker is located proximal of the side-port and wherein the proximal portion is operable to facilitate determination of a position of the catheter.

21. The catheter of claim 20, wherein the proximal portion comprises the marker band having a generally circular cross section which substantially corresponds with a cross section of the side wall of the catheter for embedding the imaging marker within the side wall.

22. The catheter of claim 16, wherein the side wall is comprised of the second material.

* * * * *